United States Patent [19]

Abdel-Monem

[11] Patent Number: 5,583,243

[45] Date of Patent: Dec. 10, 1996

[54] SALTS OF ALPHA-HYDROXY ALIPHATIC CARBOXYLIC ACIDS AND USES THEREOF

[75] Inventor: Mahmoud M. Abdel-Monem, Moscow, Id.

[73] Assignee: Zinpro Corporation, Edina, Minn.

[21] Appl. No.: 444,760

[22] Filed: May 19, 1995

[51] Int. Cl.$^6$ .................. C07F 3/06; C07F 1/08; C07F 15/02; C07F 11/00

[52] U.S. Cl. .................. 556/49; 556/31; 556/61; 556/114; 556/131; 556/147; 556/149; 562/581

[58] Field of Search .................. 556/49, 61, 31, 556/114, 131, 147, 149; 562/581

[56] References Cited

U.S. PATENT DOCUMENTS

| | | | |
|---|---|---|---|
| 2,745,745 | 5/1956 | Blake | 99/4 |
| 3,085,069 | 4/1963 | Mattison | 252/386 |
| 3,131,048 | 4/1964 | Balassa | 71/1 |
| 3,463,858 | 8/1969 | Abdel-Monem | 424/289 |
| 3,925,433 | 12/1975 | Abdel-Monem | 260/438.5 R |
| 3,941,818 | 3/1976 | Abdel-Monem | 260/429.9 |
| 3,950,372 | 4/1976 | Abdel-Monem | 260/429 R |
| 4,000,318 | 12/1976 | Ferguson et al. | 426/2 |
| 4,021,569 | 5/1977 | Abdel-Monem | 424/289 |
| 4,039,681 | 8/1977 | Abdel-Monem | 424/289 |
| 4,067,994 | 1/1978 | Anderson et al. | 424/295 |
| 4,175,121 | 11/1979 | Mantha | 424/94 |
| 4,404,408 | 9/1983 | Wirth et al. | 556/131 X |
| 4,670,269 | 6/1987 | Abdel-Monem | 426/74 |
| 4,678,854 | 7/1987 | Abdel-Monem | 556/149 |
| 4,762,854 | 8/1988 | Lloyd et al. | 514/557 |
| 4,764,633 | 8/1988 | Anderson et al. | 556/50 |
| 4,900,561 | 2/1990 | Abdel-Monem et al. | 426/2 |
| 4,912,257 | 3/1990 | Hernandez et al. | 562/581 |
| 4,948,594 | 8/1990 | Abdel-Monem et al. | 426/2 |
| 4,956,188 | 9/1990 | Anderson | 426/74 |
| 5,010,103 | 4/1991 | Kalman | 556/51 X |
| 5,061,815 | 10/1991 | Leu | 556/118 |
| 5,278,329 | 1/1994 | Anderson | 556/50 |

FOREIGN PATENT DOCUMENTS 223188  9/1957  Australia.

OTHER PUBLICATIONS

Akobe, d. Biochem. Institut d. Medizin. Fakultät d. Kaiserl. Universersität zu Osaka., s. 14–18 (1936).

*Primary Examiner*—Paul F. Shaver
*Attorney, Agent, or Firm*—Zarley, McKee, Thomte, Voorhees & Sease

[57] ABSTRACT

Novel salts are prepared wherein the cation of the salt is a divalent or trivalent cation which is an essential trace element comprising a 1:1 ratio of a complex ion formed between a trace mineral and methionine and any suitable anion, either inorganic or organic. The novel salts have the generic formula:

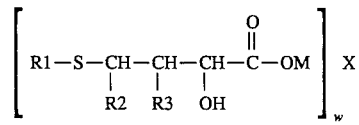

Wherein $R_1$ is methyl or ethyl, $R_2$ is hydrogen, methyl or ethyl, $R_3$ is hydrogen or methyl, M is a covalent or trivalent trace mineral cation, X is an anion and w is an integer to balance the anionic charge of X. These novel compounds are useful nutritional supplements, both for animals and humans, in that they provide a readily available source of a highly water soluble methionine which is an essential amino acid.

20 Claims, No Drawings

SALTS OF ALPHA-HYDROXY ALIPHATIC CARBOXYLIC ACIDS AND USES THEREOF

BACKGROUND OF THE INVENTION

The importance of an adequate supply of methionine to the diet of both animals and humans has long been reported in literature. Methionine is an essential amino acid needed in the building of body protein. Adequate dietary intake of methionine for swine, cattle and poultry has been known for some time to be of importance. An adequate level of methionine in the diets of swine, poultry and cattle has been shown to be important for healthy growth of the animals. Animal diets are often supplemented with DL-methionine to assure the adequacies of the sulfur amino acids content.

The DL-alpha-hydroxy analog of methionine (MHA) has been used as a substitute for DL-methionine, particularly in poultry diets. The efficacy of the alpha-hydroxy analog and its calcium salt were compared with that of DL-methionine in a chick bioassay. These studies indicated that the Ca salt of alpha-hydroxy analog is superior to the free acid and has approximately equivalent efficacy to the DL-methionine.

The synthesis of DL-alpha-hydroxy-gamma-methyl-mercapto butyric acid (the alpha-hydroxy analog of methionine) and its calcium salt were described by Blake et al. in U.S. Pat. Nos. 2,745,745 and 2,938,053 issued in May 15, 1956 and May 24, 1960, respectively. The zinc salt of alpha-hydroxy analog was also disclosed in the literature. The previously disclosed calcium and zinc salts are the diacid salts in which two molecules of the alpha-hydroxy acid are neutralized with one ion of the divalent cations of zinc or calcium. These salts are very sparingly soluble in water. The low water solubility of the salts probably decreases the bioavailability of these products as feed supplements and a water soluble compound is likely to be more bioavailable.

Accordingly, it is an object of this invention to provide novel compounds of DL-alpha hydroxy analogs of methionine wherein the DL-alpha hydroxy analogs of methionine are in a form which can be readily absorbed after ingestion by animals and readily distributed and utilized in order to provide adequate methionine levels for proper health, growth, and dietary balance of the animals.

Another object of this invention is to provide a process for making novel compounds of DL-alpha hydroxy analogs of methionine which is simple to perform and can be economically utilized in large scale plant practice to prepare the novel compounds of this invention in bulk for ready utilization in large quantities to supplement the diets of animals and humans. The method of accomplishing these and other objects will become apparent from the following description of the invention.

SUMMARY OF THE INVENTION

This invention relates to the preparation of novel salts of the alpha-hydroxy aliphatic carboxylic acids and methods of their preparation. These novel salts are the mixed anion salts with a divalent or trivalent cation which is an essential trace element. The preparation of these mixed salts requires special precautions to avoid the formation of the diacid products which are sparingly soluble in water. The mixed anion salts are characterized by high water solubility and increased bioavailability. When properly synthesized, these methionine salts function as a readily available source of methionine for dietary supplementation.

DETAILED DESCRIPTION OF THE INVENTION

It is important to note that compounds with this invention are herein referred to as "Methionine Hydroxy Acid (MHA) trace mineral complexes". These salts are to be carefully distinguished from conventional salts such as, for example, zinc sulfate and magnesium sulfate, which contain only an electrostatic attraction between the cation and the anion. The complexed salts of this invention differ from conventional salts in that while they have an electrostatic attraction between the cation and the anion, there is also a covalent bond formed between the metal and the hydroxy moiety of the hydroxy acid MHA. Methionine hydroxy acid metal complexed salts have the general formula:

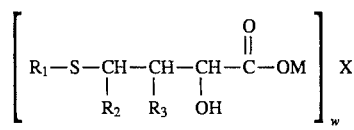

Wherein $R_1$ is methyl or ethyl, $R_2$ is hydrogen, methyl or ethyl, $R_3$ is hydrogen or methyl, M is a divalent or trivalent trace mineral cation, X is an anion and w is an integer to balance the anionic charge of X. The cation of these complex salts is represented by the bracketed material in the above formula and represents a 1:1 complex of trace mineral and alpha-hydroxy analog of methionine. Sterically, the cation moiety can be represented as follows:

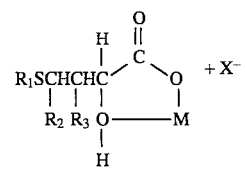

As can be seen from this formula, the five membered ring formation exists wherein the trace mineral anion is complexed by a covalent bond with a hydroxy moiety, and electrostatic attraction with the carboxylic acid moiety of the alpha hydroxy analog of methionine. In addition, the complex is formed by a 1:1 ratio of the alpha hydroxy analog of methionine molecules and trace mineral anions with each trace mineral anion becoming complexed with one MHA molecule. The preparation of these mixed salts require special precautions to avoid the formation of the diacid products which are sparingly soluble in water. The mixed anion salts are characterized by high water solubility and increased bioavailability, thus providing effective utilization of the methionine analog.

In the above-described formula, X represents the anion. The selection of an anion is not critical. The anion can be an inorganic anion, an organic anion, a monovalent anion, a divalent anion, or a polyvalent anion. However, in order to have the molecules of the salt balanced electrostatically, w is a whole number integer to balance the anionic charge of the anion X.

Preferably, the source of the anion, X, is an inorganic acid. Suitable inorganic anions can be found in the halogen acids family, the sulfates, and the phosphates. Preferably, where the anion is an inorganic anion, it is selected from the group consisting of monovalent anions, such as halides, hydrogen sulfate, and dihydrogen phosphates. Utilization of monovalent anions selected from the above group is preferred because of increased solubility and because of the readily available sources of common inorganic anions such as the halides, hydrogen sulfate, and dihydrogen phosphate. Most preferably, the anion is selected from the group consisting of chloride and hydrogen sulfate or acid sulfate, the latter two terms being utilized herein interchangeably.

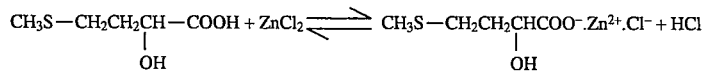

As heretofore briefly mentioned, the anion can also be an organic anion moiety derived from an organic acid. It can be derived from simple aliphatic carboxylic acids, both monobasic carboxylic acids and dibasic carboxylic acids. For example, the anion can be acetate or propionate, or where the acid is a dibasic acid, succinate or adipate. In addition, the acid source can be substituted aliphatic acids, both monobasic and dibasic, such as, for example, chloroacetic acid. The acid source of the anion may also be aromatic acids such as, for example, benzoic acid. It can also be aralkyl acids, both substituted and unsubstituted. Where organic acid sources are utilized as the source of the anion for the salts of this invention, it is preferred that the source be a monobasic carboxylic acid and that the acid be either acetic acid, propionic, or benzoic.

In the above-described formula, M represents a covalent or trivalent trace mineral cation. Preferred trace mineral cations include zinc, copper, manganese, iron and chromium.

An important feature of the 1:1 complex salts, having alpha hydroxy analog of methionine and trace mineral complexes as a cation and associated with suitable anions, is that the salts formed are superior to previously known alpha-hydroxy diacid salts due to increased water solubility for potentially increased bioavailability in animals.

The following examples are offered to further illustrate the product and process of this invention. They are not intended to limit the scope of the invention in any manner.

EXAMPLE 1

Alpha-Hydroxy-Gamma Methyl-Mercapto Butyric Acid Zinc Chloride (Alpha Hydroxy Methionine Zinc chloride)

Method 1

One molar equivalent of the hydroxy acid was added to one molar equivalent of zinc oxide. Hydrochloride acid solution was added slowly with heating and mixing until the zinc oxide completely dissolved. Only one molar equivalent of Hydrochloric acid was required. Additional two-tenth of a molar equivalent (20 percent) were required to adjust the pH to assure the stability of the mixed salt in solution.

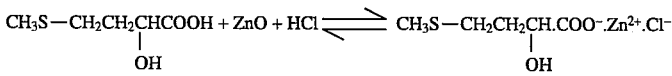

Method 2

One molar equivalent of the hydroxy acid was mixed with a solution of one molar equivalent of zinc chloride. A clear solution was formed. The solution was concentrated under reduced pressure and the distillate was carefully collected. The distillate was titrated with standard solution of potassium hydroxide using phenolphthalein as indicator. Sixtenth of a molar equivalent of hydrochloric acid (60 percent of theory was recovered). Further distillation indicated that additional hydrochloric acid was slowly obtained.

Method 3

The pH of 1.0, 0.1 and 0.01M solutions of the alpha-hydroxy acid, and a mixture of alpha hydroxy acid and zinc chloride were measured and listed in the following table:

|  | pH at 25° C. | | |
| --- | --- | --- | --- |
|  | 1.0M | 0.1M | 0.01M |
| Alpha-hydroxy Acid | 2.21 | 2.62 | 3.05 |
| Mixture of Alpha-hydroxy Acid and Zinc Chloride | 1.19 | 2.08 | 3.04 |

The alpha-hydroxy acid is a partially dissociated acid. A ten-fold dilution of its solution results in a change of approximately 0.5 pH units. However, when the alpha hydroxy acid is mixed with zinc chloride, the mixed salt is formed in addition to a one molar equivalent of hydrochloric acid. The released hydrochloric acid is a strong (completely dissociated) acid. A ten-fold dilution of a solution of a strong acid is expected to result in a change of approximately 1.0 pH units. The results in the table confirms this conclusion.

EXAMPLE 2

Alpha-Hydroxy-Gamma Methyl-Mercapto Butyric Acid Copper Hydrogensulfate

Method 1

A solution of a one molar equivalent of alpha-hydroxy acid was added dropwise to a solution of one molar equivalent of copper sulfate. The deep blue color of the copper sulfate slowly changed to greenish and then deep green color. The change of the color of the copper solution indicates the complex formation between the Cu++ cation and the hydroxy carboxylic acid.

Method 2

One molar equivalent of alpha-hydroxy acid was mixed with a solution of one molar equivalent of copper sulfate. The solution was mixed with a soluble carrier and dried using a spray dryer. A sample of the product was extracted with Absolute Methanol. The Methanol removed all the green colored product and left the inert carrier behind. The methanol extract was evaporated to dryness to give a homogenous green powder. The residue was dissolved in methanol, filtered and the filtrate evaporated to dryness. The green homogenous product was collected and analyzed.

Method 3

One molar equivalent of copper oxide was added to a solution of one molar equivalent of alpha-hydroxy acid in water. The copper oxide was only partially soluble. A solution of hydrochloric acid was added. Only one molar equivalent of hydrochloric acid was required for complete solubilization of the copper oxide. Additional hydrochloric acid (two-tenth of a molar equivalent or 20 percent) was required to adjust the pH to assure the stability of the mixed salt formed.

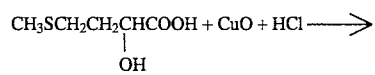

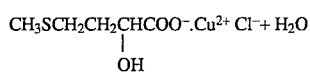

EXAMPLE 3

Alpha-Hydroxy-Gamma Methyl-Mercapto Butyric Acid Ferric Chloride

Method 1

One molar equivalent of alpha-hydroxy acid was added to a solution of one molar equivalent of ferric chloride. The mixture was heated with stirring to from a clear solution. The solution was concentrate under reduced pressure. The distillate was carefully collected and titrated with a standard solution of potassium hydroxide using phenolphthalein as indicator. Approximately 65 percent of the theoretical amount of acid was collected. The residue of the mixed salt was diluted with water and the distillation continued to provide additional 10 percent of the acid.

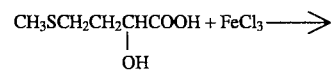

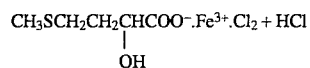

The mixed salts described in this application are more bioavailable forms of the sulfur amino acid and the trace element. The salts are readily soluble in water and relatively stable at the pH of the gut contents of animals. The cation of the trace element is expected to be present in the form of a complex with the alpha-hydroxy acid. The remaining valencies of the coordinate sphere will be occupied by the counter anion and water as shown in the following formula for the copper complex.

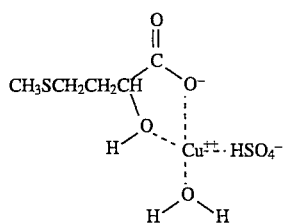

EXAMPLE 4

Preparation of Zinc Alpha-Hydroxy-Gamma-Methyl-Mercapto-Butyrate Chloride

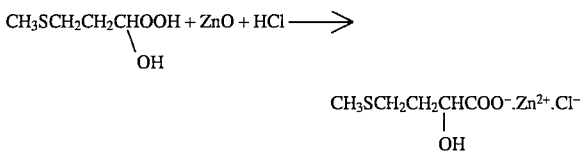

Zinc Oxide (8.14 g, 0.1 mole) was added to a beaker containing distilled water. Concentrated hydrochloric Acid (10 g, 0.1 mole) was added and mixed well. Alpha-hydroxy-gamma-methyl-mercapto butyric acid (17.07 g of 88 percent solution, 0.1 mole) was added. The mixture was heated to boiling. A clear solution was obtained. Upon standing a precipitate began to form additional hydrochloric acid (0.03 mole) was added and a clear solution was obtained that was stable on standing. Concentration of the solution have an oily residue that was readily soluble in water.

EXAMPLE 5

Preparation of Copper Alpha Hydroxy-Gamma-Methyl-Mercapto Butyric Chloride

Method 1

Copper oxide (8.49 g, 0.1 mole) was added to a solution of alpha-hydroxy-gamma-methyl-mercapto butyric acid (17.07 g of 88 percent solution, 0.1 mole). The mixture was heated and 6M hydrochloric acid solution was added dropwise. After 17 mL (0.1 mole) were added, most of the precipitate had dissolved. An additional 3 mL was added to obtain a clear dark green solution. The solution was filtered and only traces of copper oxide were remaining. The filtrate was evaporated to dryness to give a sticky residue. The residue was completely soluble in water and absolute methanol.

Method 2

285 pounds of copper sulfate pentahydrate ($CuSO_4.5H_2O$) was added to 1000 pounds of hot water (190°–200° F.). After all the copper sulfate had dissolved, 195 pounds of 88% solution of alpha-hydroxy-gamma-methyl-mercapto-butyric acid was added slowly with continued mixing and stirring. After several minutes, a dark green solution was formed. 400 pounds of a water soluble carrier (maltodextrin) was added to the solution. After all the carrier had dissolved, the resulting solution was spray dried using a sonic impulse drier. A green powder was obtained. This powder was found to be very water soluble. Analysis of this product found 9% Cu.

EXAMPLE 6

Preparation of Ferric Alpha-Hydroxy-Gamma-Methyl-Mercapto Butyrate Chloride

A solution of alpha-hydroxy-gamma-methyl-mercapto butyric acid (17.07 g of 88 percent of solution, 0.1 mole) in water (30 ml) was added to a solution of ferric chloride (27.03 g of $FeCl_3.6H_2O$, 0.1 mole) in water (30 ml). The mixture was heated with stirring until clear. The mixture was concentrated under reduced pressure. The distillate was collected and titrated with 0.1N potassium hydroxide using phenolphthalein as indicator. 62 mL of 0.1N potassium hydroxide was required. The residue was diluted with 100 mL of water and further concentrated under reduced pressure. The distillate was titrated and required 7.2 mL of 0.1N potassium hydroxide. The residue of the ferric salt in the distillation flask was dark reddish brown and was completely soluble in water.

EXAMPLE 7

Preparation of Mixed Manganese-Zinc Alpha-Hydroxy-Gamma-Methyl Mercapto Butyrate Chloride Manganese chloride (9.90 g, 0.05 mole) and zinc chloride (6.82 g, 0.05 mole) were added to water (50 ml) in a beaker. The mixture was stirred with mild warming to give a clear solution. A solution of alpha-hydroxy-gamma methyl mercapto butyric acid (17.07 g, 0.1 mole) in water (50 ml) was added dropwise to the zinc chloride and manganese chloride solution. Stirring and heating were continued until a clear solution was obtained. The solution was evaporated to dryness. The residue was completely soluble in water.

Based on the above examples, it can be appreciated that compounds prepared in accordance with the method of the present invention have high water solubility in comparison with previously disclosed calcium and zinc diacid salts of alpha-hydroxy acid. Thus, these compounds are expected to have superior bioavailability as feed supplements. Poultry testing is underway. It is therefore seen that the invention accomplishes at least all of its stated objectives.

What is claimed is:

1. Novel salts of alpha-hydroxy aliphatic carboxylic acids having the general formula:

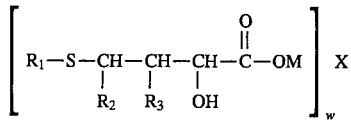

Wherein $R_1$ is methyl or ethyl, $R_2$ is hydrogen, methyl or ethyl, $R_3$ is hydrogen or methyl, M is a cation, X is an anion, and w is a whole number integer to balance the anionic charge of the anion X.

2. A novel salt of claim 1 wherein the cation is an essential trace element.

3. A novel salt of claim 2 wherein the cation is selected from the group consisting of zinc, copper, manganese, iron, and chromium.

4. A novel salt of claim 2 wherein the cation is zinc.

5. A novel salt of claim 2 wherein the cation is cuprous or cupric.

6. A novel salt of claim 2 wherein the cation is ferrous or ferric.

7. A novel salt of claim 2 wherein the cation is manganese.

8. A novel salt of claim 1 wherein the anion is an inorganic anion.

9. A novel salt of claim 1 wherein the anion is an organic anion.

10. A novel salt of claim 8 wherein the anion is chloride.

11. A novel salt of claim 1 wherein the cation is a trivalent cation.

12. A novel salt of claim 1 wherein the cation is a divalent cation.

13. Trace mineral methionine complexed salts having the general formula:

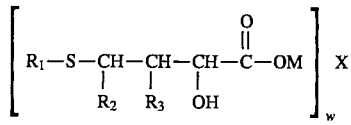

wherein X is an inorganic anion selected from the group consisting of halides, sulfates, and phosphates, M is a trace mineral cation, and w is an integer to balance the anionic charge of X.

14. A method of preparing alpha-hydroxy aliphatic carboxylic acids comprising:
adding together a metal salt to an equivalent amount of alpha-hydroxy-gamma-methyl-mercapto butyric acid to provide a reaction mixture, and heating said reaction mixture at a temperature higher than room temperature but not exceeding the boiling point of said reaction mixture.

15. Zinc alpha-hydroxy-gamma-methyl-mercapto-butyrate chloride.

16. Copper alpha hydroxy-gamma-methyl-mercapto butyrate chloride.

17. Ferric alpha-hydroxy-gamma-methyl-mercapto butyrate chloride.

18. Manganese-zinc alpha-hydroxy-gamma-methyl-mercapto butyrate chloride.

19. The process of claim 14, wherein the reaction is conducted in the presence of water.

20. The process of claim 14, wherein the amount of metal salt and alpha-hydroxy-gamma-methyl-mercapto butyric acid employed are equimolar quantities.

* * * * *